(12) United States Patent
Ladd

(10) Patent No.: US 6,679,840 B1
(45) Date of Patent: Jan. 20, 2004

(54) PATIENT MONITOR

(76) Inventor: Leland L. Ladd, P.O. Box 8189, Sylvania, OH (US) 43560

( * ) Notice: Subject to any disclaimer, the term of this patent is extended or adjusted under 35 U.S.C. 154(b) by 264 days.

(21) Appl. No.: 09/677,365

(22) Filed: Oct. 2, 2000

Related U.S. Application Data

(60) Provisional application No. 60/156,856, filed on Sep. 30, 1999.

(51) Int. Cl.[7] .................................................. A61B 5/00
(52) U.S. Cl. ...................................................... 600/300
(58) Field of Search .................................. 600/300, 301, 600/302, 303, 304, 305, 306, 307, 308, 309; 128/902, 903, 904; 340/573.1; 424/2; 434/258

(56) References Cited

U.S. PATENT DOCUMENTS

| | | | |
|---|---|---|---|
| 3,949,753 A | | 4/1976 | Dockhorn |
| 4,633,237 A | | 12/1986 | Tucknott et al. |
| 4,676,776 A | | 6/1987 | Howson |
| 4,810,243 A | | 3/1989 | Howson |
| 5,121,107 A | | 6/1992 | Newell |
| 5,147,310 A | | 9/1992 | Giannini et al. |
| 5,558,638 A | | 9/1996 | Evers et al. |
| 5,563,584 A | | 10/1996 | Rader et al. |
| 5,573,506 A | | 11/1996 | Vasko |
| 5,582,601 A | | 12/1996 | Wortrich et al. |
| 5,590,648 A | * | 1/1997 | Mitchel et al. ............. 128/630 |
| 5,658,250 A | | 8/1997 | Blomquist et al. |
| 5,673,691 A | * | 10/1997 | Abrams et al. ............. 128/630 |
| 5,683,367 A | | 11/1997 | Jordan et al. |
| 5,687,734 A | * | 11/1997 | Dempsey et al. ............ 128/696 |
| 5,792,109 A | | 8/1998 | Ladd |
| 5,957,838 A | * | 9/1999 | Rantala ....................... 600/300 |
| 5,967,975 A | * | 10/1999 | Rideway ...................... 600/300 |
| 6,029,078 A | * | 2/2000 | Weinstein et al. ........... 600/407 |
| 6,050,940 A | * | 4/2000 | Braun et al. ................. 600/300 |
| 6,375,614 B1 | * | 4/2002 | Braun et al. ................. 600/300 |

FOREIGN PATENT DOCUMENTS

| | | |
|---|---|---|
| WO | WO 88/07384 | 10/1988 |
| WO | WO 94/11054 | 5/1994 |

\* cited by examiner

*Primary Examiner*—Daniel Robinson

(57) ABSTRACT

A patient monitor has an information processor, an information display, a control or selector, at least two sensor sockets, and at least two patient sensors. The information processor is programmable and re-programmable according to a user's requirements. The sockets are substantially identical with a number of socket connectors and are electrically connected in parallel with one another. One of the sensors monitors one aspect of a patient's condition and generates a signal to the information processor accordingly. A second sensor monitors a second aspect of a patient's condition and generates a signal to the information processor accordingly. Each of the patient sensors plugs into any of the sensor sockets. The sensor sockets and the sensors have connectors that connect when the sensors are plugged into the sockets. Not all of the connectors are used by a sensor, however, so the patient monitor identifies and differentiates each sensor not by which socket it is plugged into, but by which plug and socket connectors are used.

2 Claims, 12 Drawing Sheets

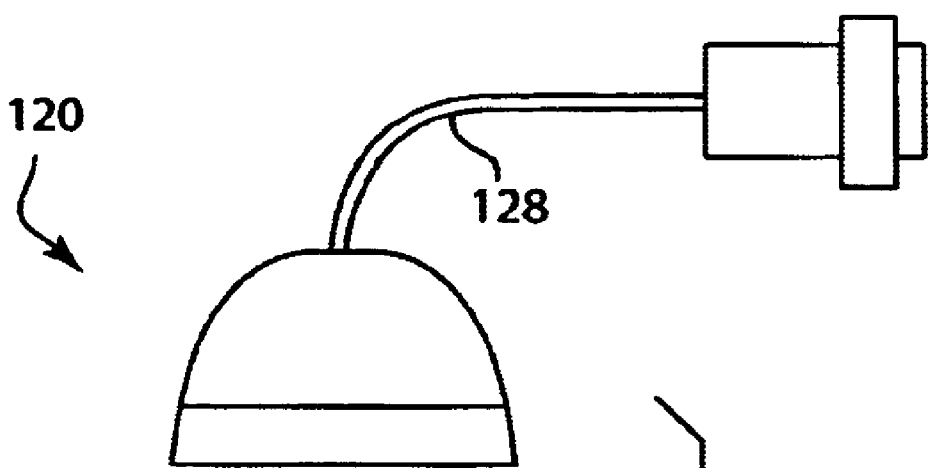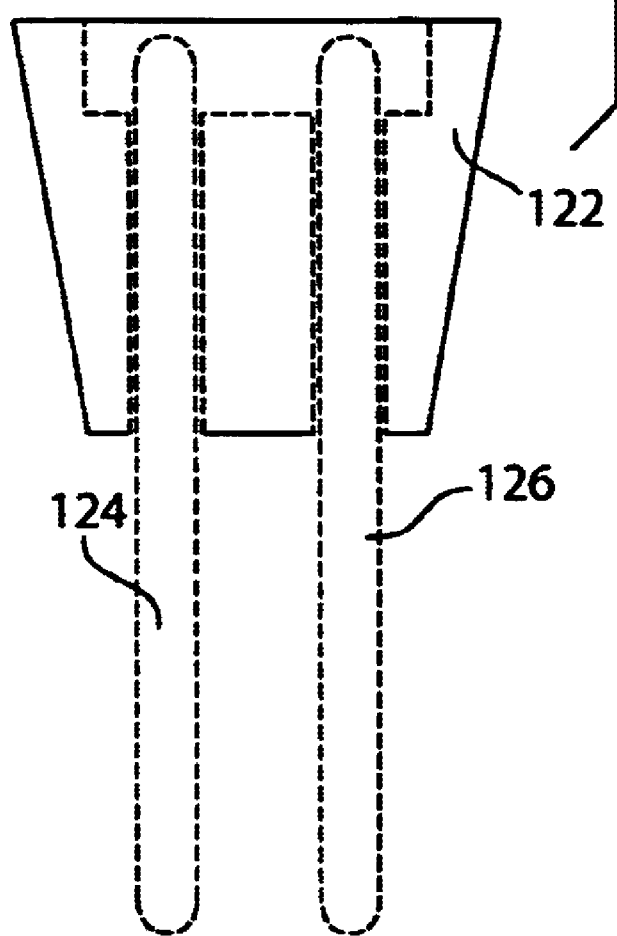
FIG. 11

PATIENT MONITOR

CROSS-REFERENCES TO RELATED APPLICATIONS

This is a continuing application of co-pending United States provisional Patent Application Serial No. 60/156,856, entitled Patent Monitor and filed on Sep. 30, 1999 by Leland L. Ladd, the disclosure of which is incorporated here by reference.

STATEMENT REGARDING FEDERALLY SPONSORED RESEARCH OR DEVELOPMENT

Not Applicable.

BACKGROUND OF THE INVENTION

The invention relates generally to patient care and more particularly to the monitoring of a patient's condition. and the issue of an alarm when a predetermined criteria is met.

A variety of personal condition indicators may require monitoring in various patient care settings, including home care, nursing home, and hospital environments. Consistent quality monitoring is frequently compromised, however, in each setting. In a home setting, trained personnel are typically not available or affordable, for example, and care can easily be overlooked. Similarly, trained nursing care personnel are commonly limited in a nursing home setting. This may result from limited funding or cost reduction pressures. This may also result from unusual or unforeseen circumstances in which more patients require attention from trained personnel at a given time than was expected or forecasted. That is to say, merely the inherent unpredictability of nursing care may result in a personnel short fall.

Even in a hospital setting, personnel resources may fall short for some, if not all, of the same reasons as noted above. Further, the demands of an operating theatre can cause a lapse in patient monitoring. To say the very least, any effective assistance that may facilitate or enhance the work of an operating room nurse is clearly desirable. Even the smallest detail can make a life or death difference in surgery, including not requiring the time to identify which of several sockets on a piece of equipment is the correct socket, for example.

BRIEF SUMMARY OF THE INVENTION

Accordingly, a patient monitor of the invention has an information processor, an information display, a control or selector, at least two sensor sockets, and at least two patient sensors. The sockets are substantially identical with a number of socket connectors and are electrically connected in parallel with one another. One of the sensors monitors one aspect of a patient's condition and generates a signal to the information processor accordingly. A second sensor monitors a second aspect of a patient's condition and generates a signal to the information processor accordingly. Each of the patient sensors plugs into any of the sensor sockets. The sensor sockets and the sensors have connectors that connect when the sensors are plugged into the sockets. Not all of the connectors are used by a sensor, however, so the patient monitor identifies and differentiates each sensor not by which socket it is plugged into, but by which plug and socket connectors are used.

These and other features, objects, and benefits of the invention will be recognized by one having ordinary skill in the art and by those who practice the invention, from the specification, the claims, and the drawing figures.

BRIEF DESCRIPTION OF THE SEVERAL VIEWS OF THE DRAWING

FIG. 11 is a schematic view of a fluid level sensor for the patient monitor;

DETAILED DESCRIPTION OF THE INVENTION

Figure 1:
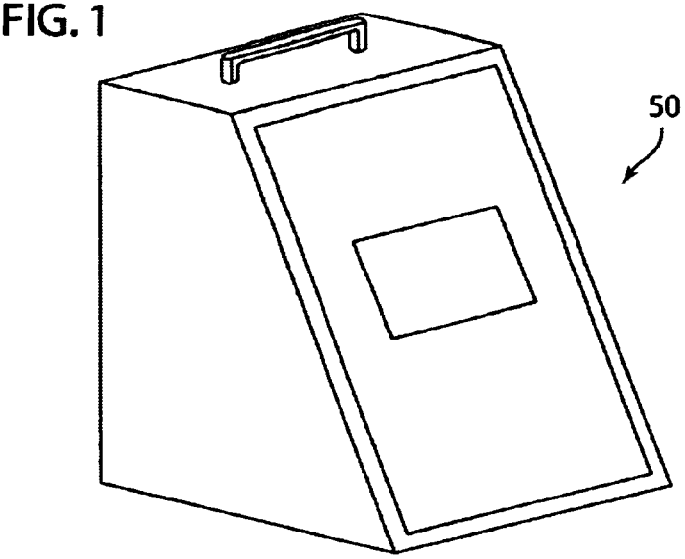
FIG. 1 is a front perspective view of a cabinet of a patient monitor according to the invention.
Figure 2:
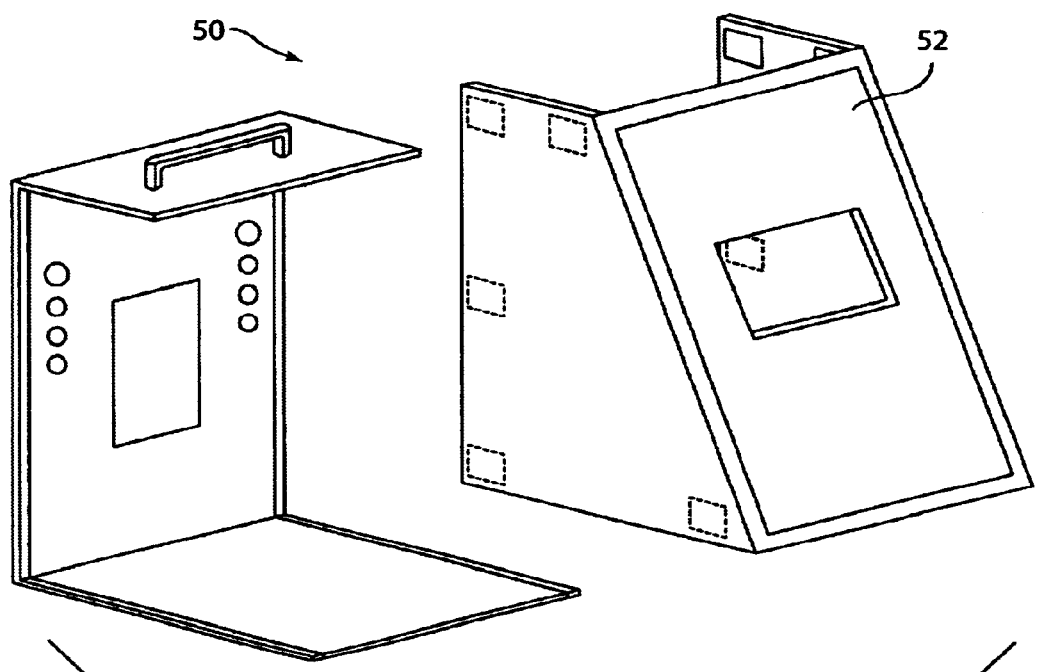
FIG. 2 is an exploded view thereof.
Figure 3:
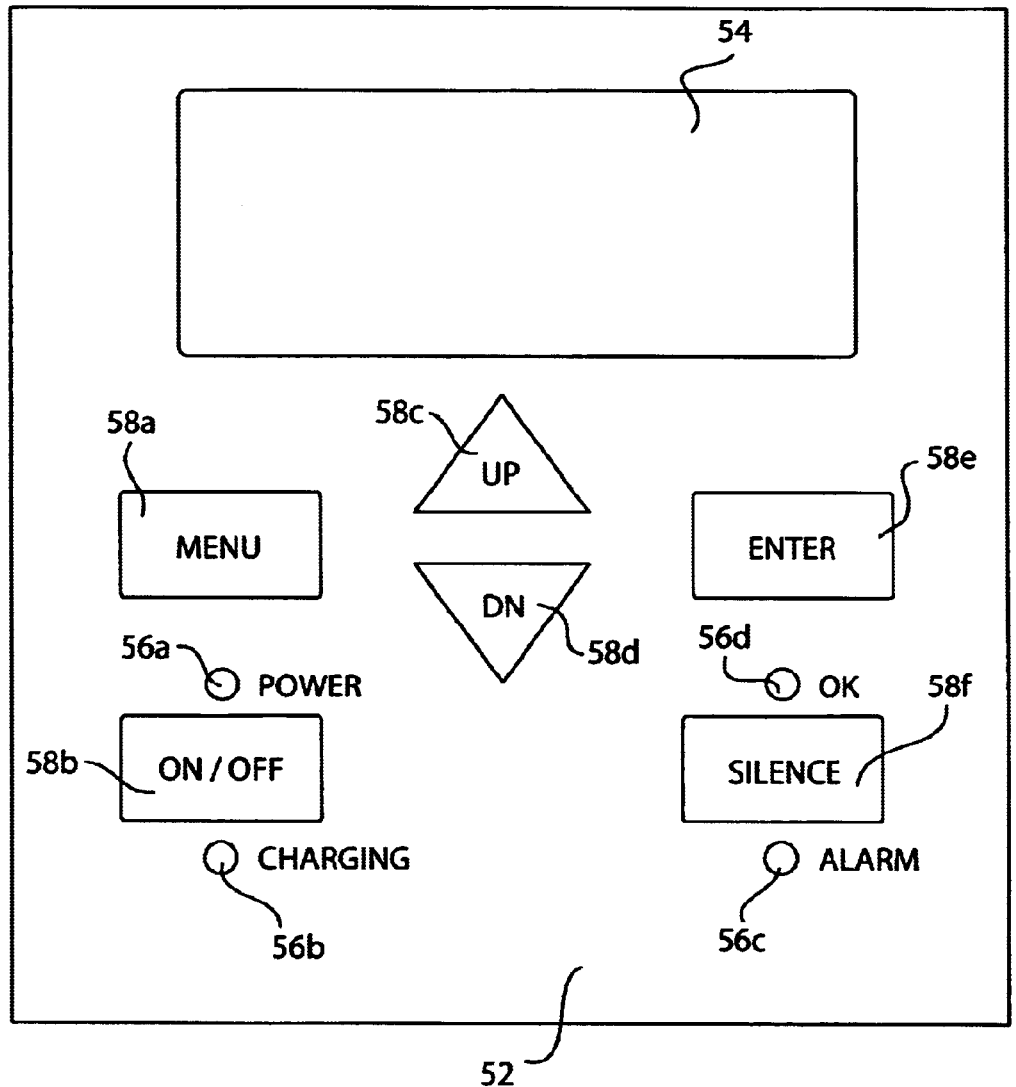
FIG. 3 is a projection of the front panel thereof, showing a preferred user interface.

A preferred embodiment of a patient monitor according to the invention is generally shown in the drawing figures and discussed below. The patient monitor may be generally housed in a cabinet 50 as shown in drawing FIGS. 1–3. The cabinet may have a front panel 52 with an alpha-numeric display panel 54, status indicators 56a–56d, and user input switches 58a–58f. The cabinet 50 may be of various constructions and configurations, as will be understood by one having ordinary skill in the art. Some exemplary cabinet materials may include, without limitation, stainless steel, powder coated metals, and engineering plastics.

The alpha-numeric display panel 54 is preferably a liquid crystal display (LCD) although other display devices may be used depending upon a manufacturer's or user's preferences. More particularly, the inventor has found a 16×2 character LCD to perform well in the patient monitor.

Likewise, light emitting diodes have been found to perform well for the various status indicators 56a–56d, although other indicators may be substituted. Presently, indicators for monitor power status (on/off) 56a, for batter power source charging status 56b, and for an alarm condition 56c and 56d relative to a patient monitor have been found to be sufficient and minimally required indicators. Additional indicators may be added and desired by various users, although potential users are cautioned against the inherent confusion that comes with a plethora of indicators.

A sufficient and minimal array of input switches is also shown in the drawings and includes switches for menu access 58a, power 58b, menu scrolling 58c and 58d, menu choice entry 58e, and alarm toggle 58f. Membrane tactile switching or the like is preferred if only because of the ease with which the front panel may be wiped clean. Other switching may also be used with compromises in the ability to clean the front panel around the switches, however. While most of the switches are most preferably accessible on the front panel, the power switch 58b may alternatively be relocated on the back panel, for example.

Figure 4:
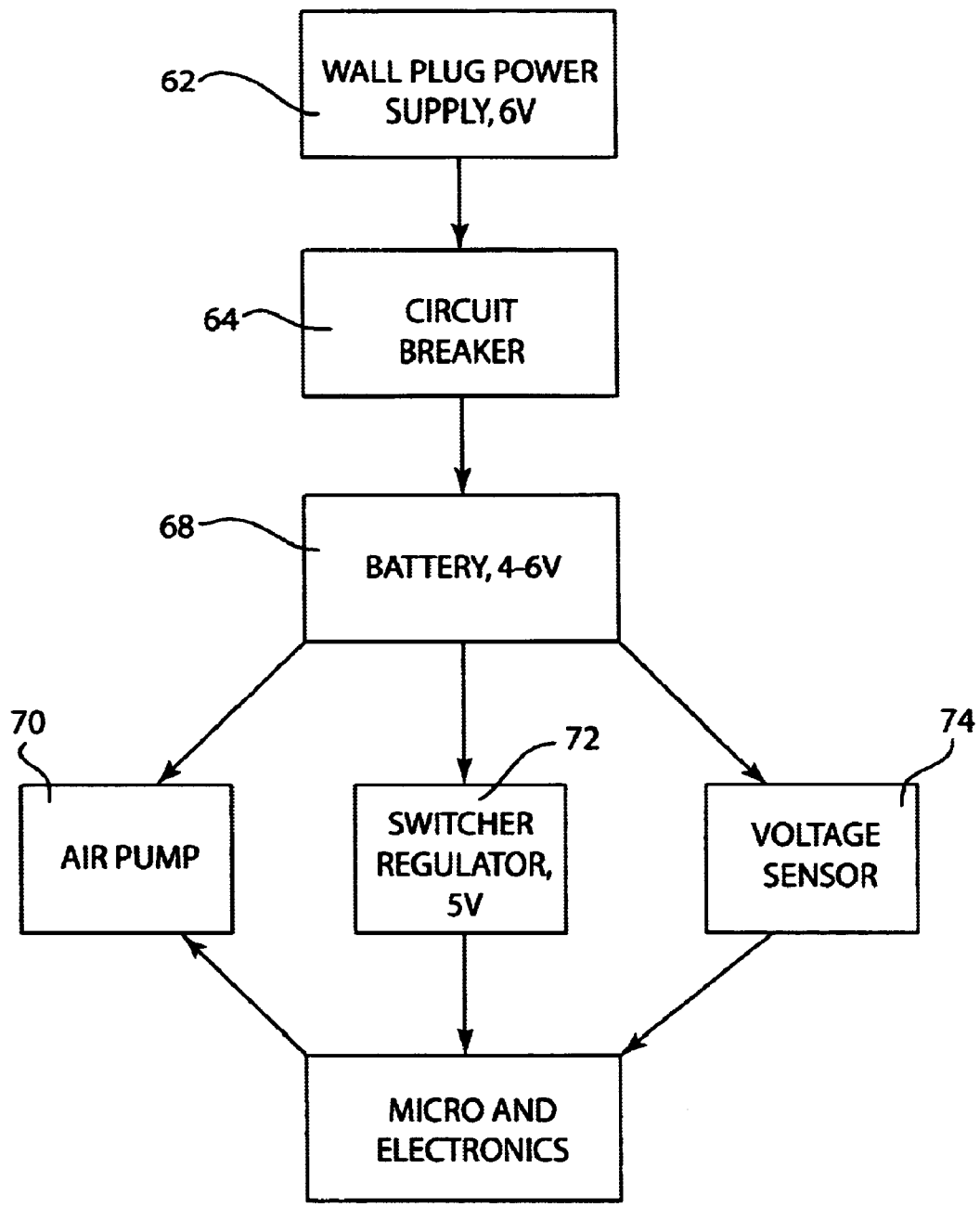
FIG. 4 is a block diagram of a power circuit for the patient monitor.

The monitor is preferably provided with an alternative choice between wall plug, also commonly known as line power, and an onboard battery power supply (FIG. 4). A power cord with an integral transformer and plug may be used as is commonly known to provide an about six volt battery current to the patient monitor. By providing onboard battery power, the patient monitor may operate a nominal twenty-five hours during a power failure or patient transportation, for example.

A circuit for the ability to choose alternative power sources is schematically shown in FIG. 4. The transformer power cord 62 feeds through a circuit breaker 64 to the battery 66. The battery 68 then feeds to an air pump 70, a power regulator 72, and a voltage sensor 74. The power regulator may be a switching type regulator of about five volts output, for example. The output of the regulator is then used for the electronics 80 of the patient monitor. A loop from the battery 68 to the voltage sensor 74 provides monitoring of the power supply and may send a low power signal to the control electronics 80 when battery power drops below a preselected value, as will be understood by one having ordinary skill in the art. This may occur after an extended period of being disconnected from wall power. A low power signal alarm may be interpreted as a flashing power indicator 56a or an audible voice alert. The low power alarm will preferably activate at power levels of about twenty-five percent, at fifteen percent, and again at five percent remaining charge. These power levels may be reflected in the power indicator 56a as increasing flashing frequency. The voice alarm may be programmed to state the power level that remains.

Figure 5:
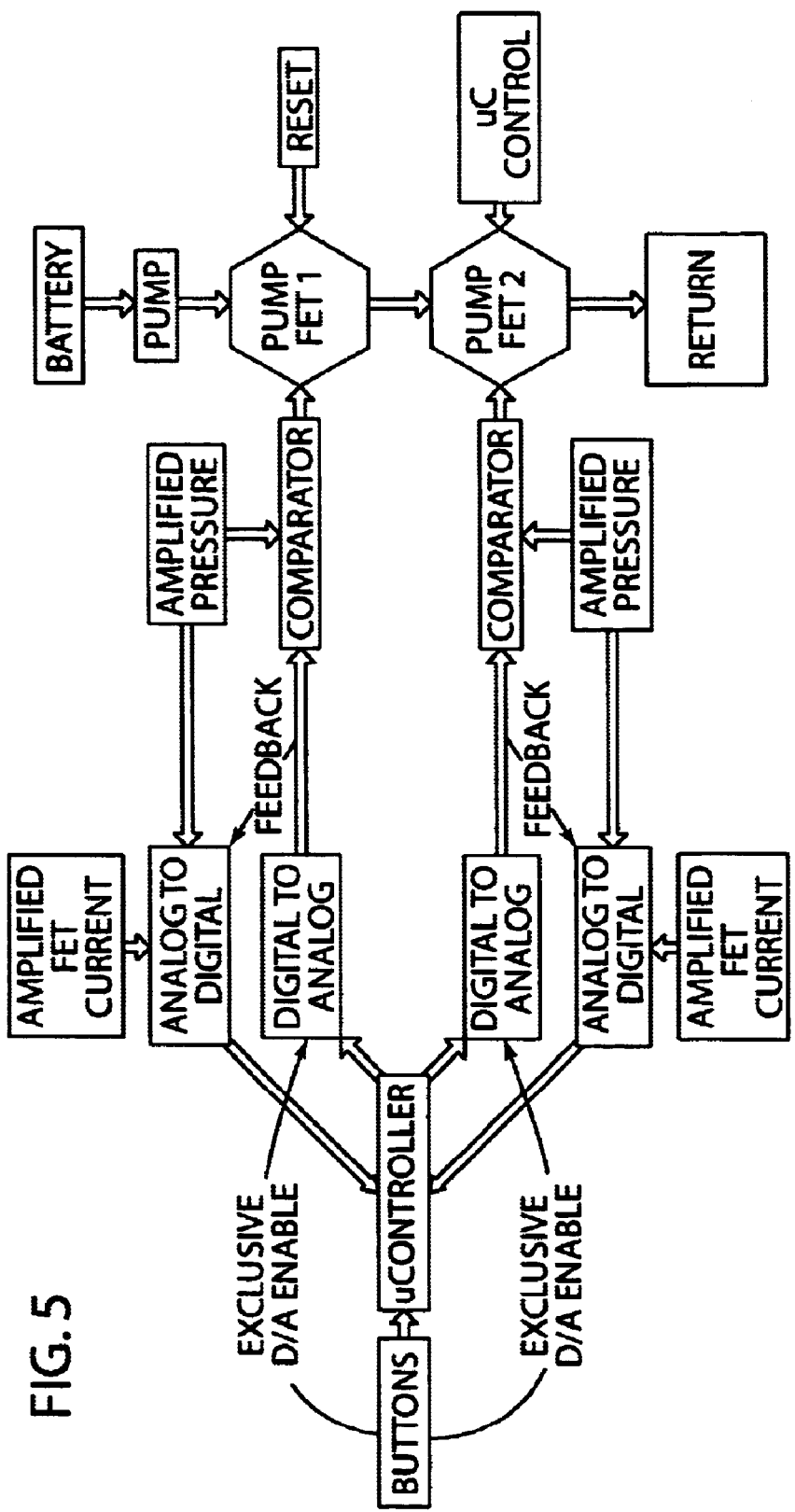
FIG. 5 is a pump control diagram for the patient monitor.
Figure 6:
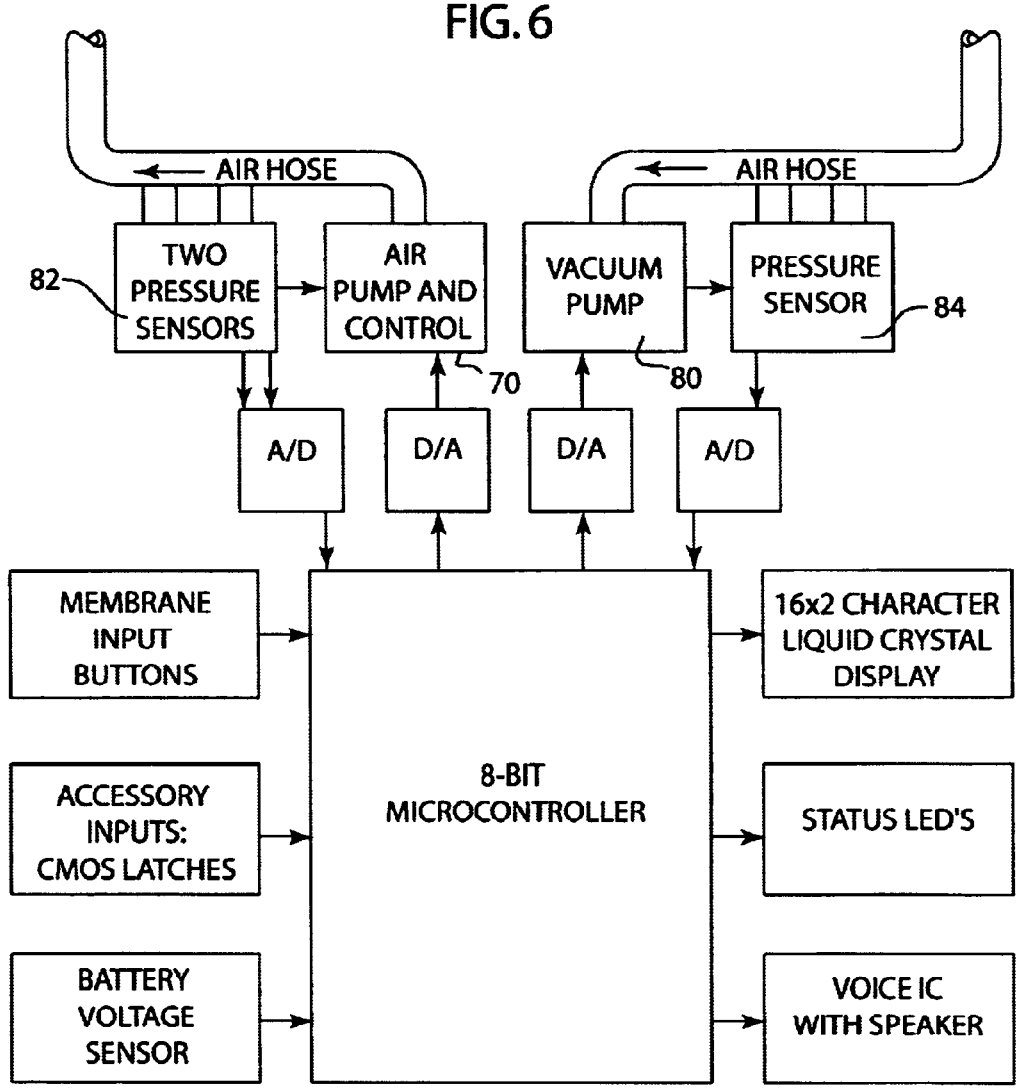
FIG. 6 is a block diagram of a circuit therefor.
Figure 7:
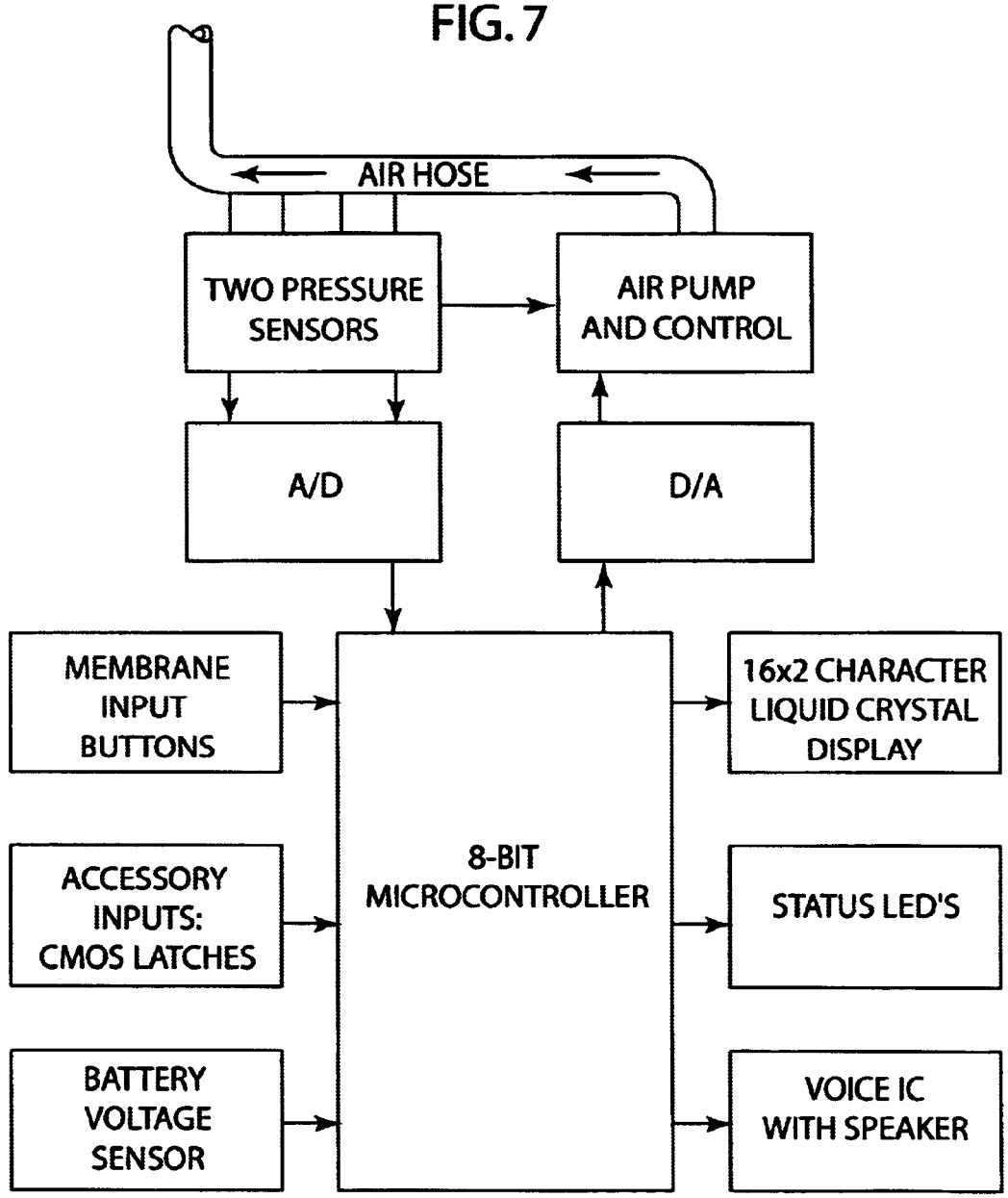
FIG. 7 is the view of FIG. 6 showing an alternative circuit.
Figure 8:
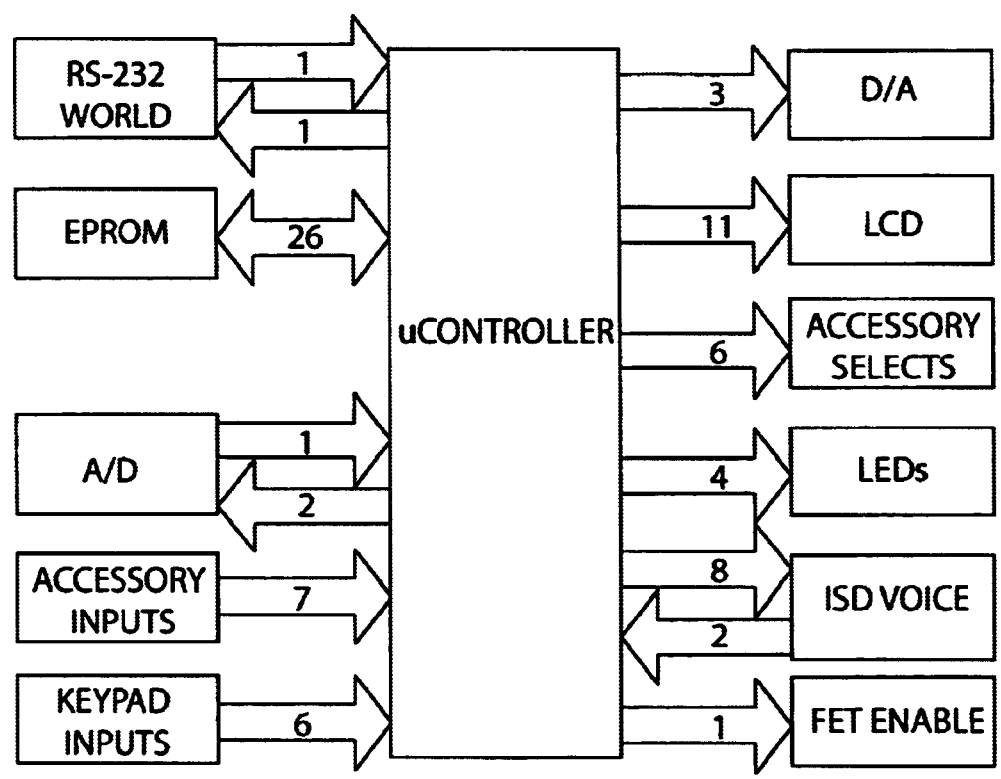
FIG. 8 is a block diagram of a processor circuit for the patient monitor.
Figure 9:
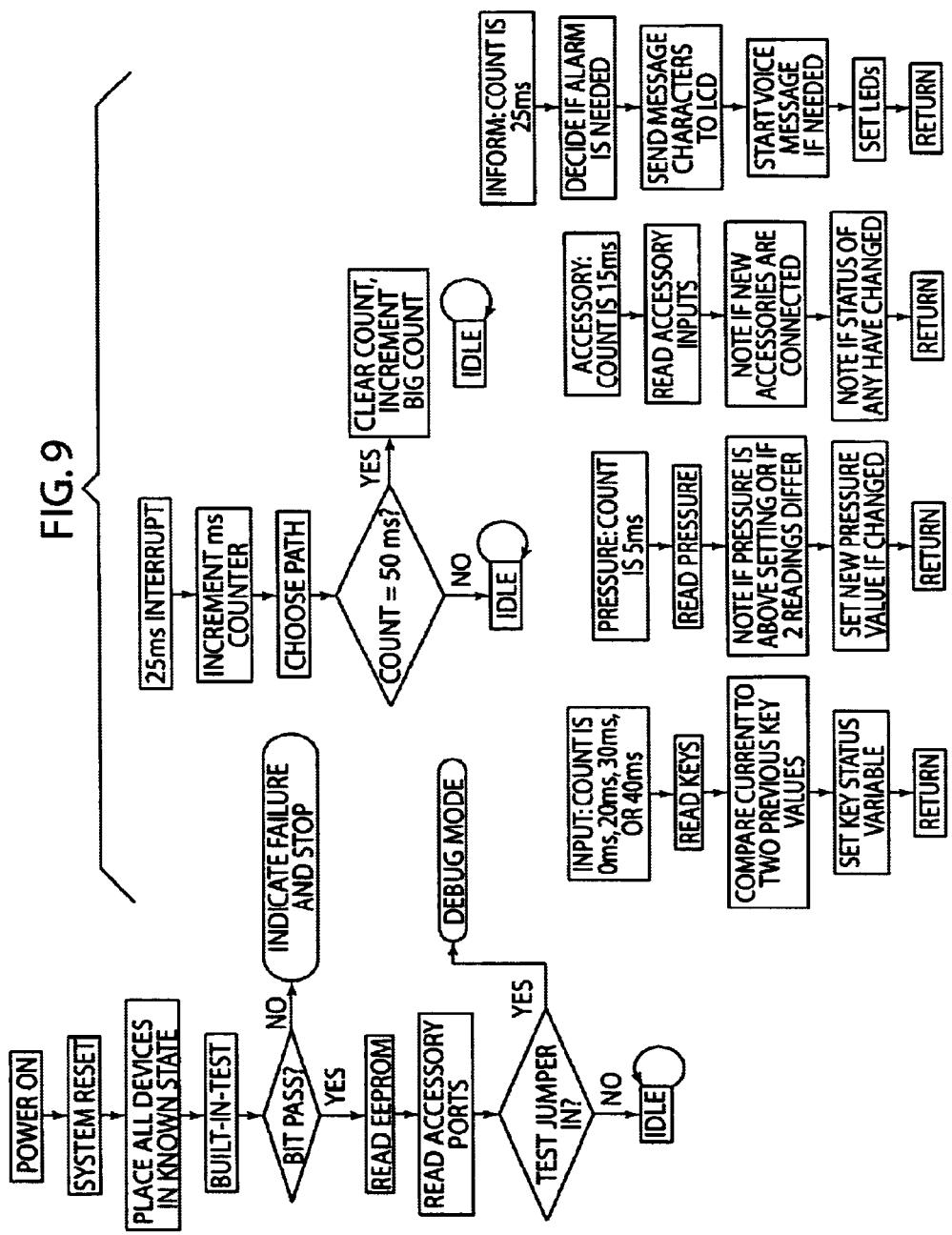
FIG. 9 is a software flow diagram for the patient monitor.

The patient monitor is preferably provide with an air pressure pump 70 and may also have a vacuum pump 80 (FIGS. 5–7). Alternatively, a manufacturer or user may prefer to omit the vacuum pump 80 or the pressure pump 70, depending upon their monitoring requirements (FIG. 7).

The pressure pump 70 is useful with infusion bags and may provide a capacity of about 500 mm Hg pressure by connection of an infusion bag air pressure tube with an air pressure connector of the patient monitor. Dual redundant air pressure sensors 82 are preferably used to monitor selected and used air pressure within about five percent of a predetermined setting. The patient monitor may further be programmed to facilitate a pressure tubing alarm. The pressure tubing alarm may sense a blocked or kinked tube when a set pressure is achieved too quickly. Conversely, an open or leaking pressure tube may be sensed when a set pressure takes too long to achieve. Further, a pressure tubing alarm may be set for when either an infusion bag fluid tube or a pressure tube becomes blocked or kinked after a set pressure is properly achieved.

Similarly, the vacuum pump 80 is useful with suction canisters by connection of a canister suction tube with a suction connector of the patient monitor. A vacuum sensor 84 monitors the selected and used vacuum level within about five percent of a predetermined setting. The patient monitor may also be programmed to facilitate vacuum tubing alarms. The vacuum tubing alarm may sense a blocked or kinked tube when a set vacuum is achieved too quickly. Conversely, an open or leaking tube may be sensed when a set vacuum takes too long to achieve. Further, a vacuum alarm may be set if either a suction canister tube or a vacuum tube becomes block or kinked after a set pressure is properly achieved.

Figure 10:
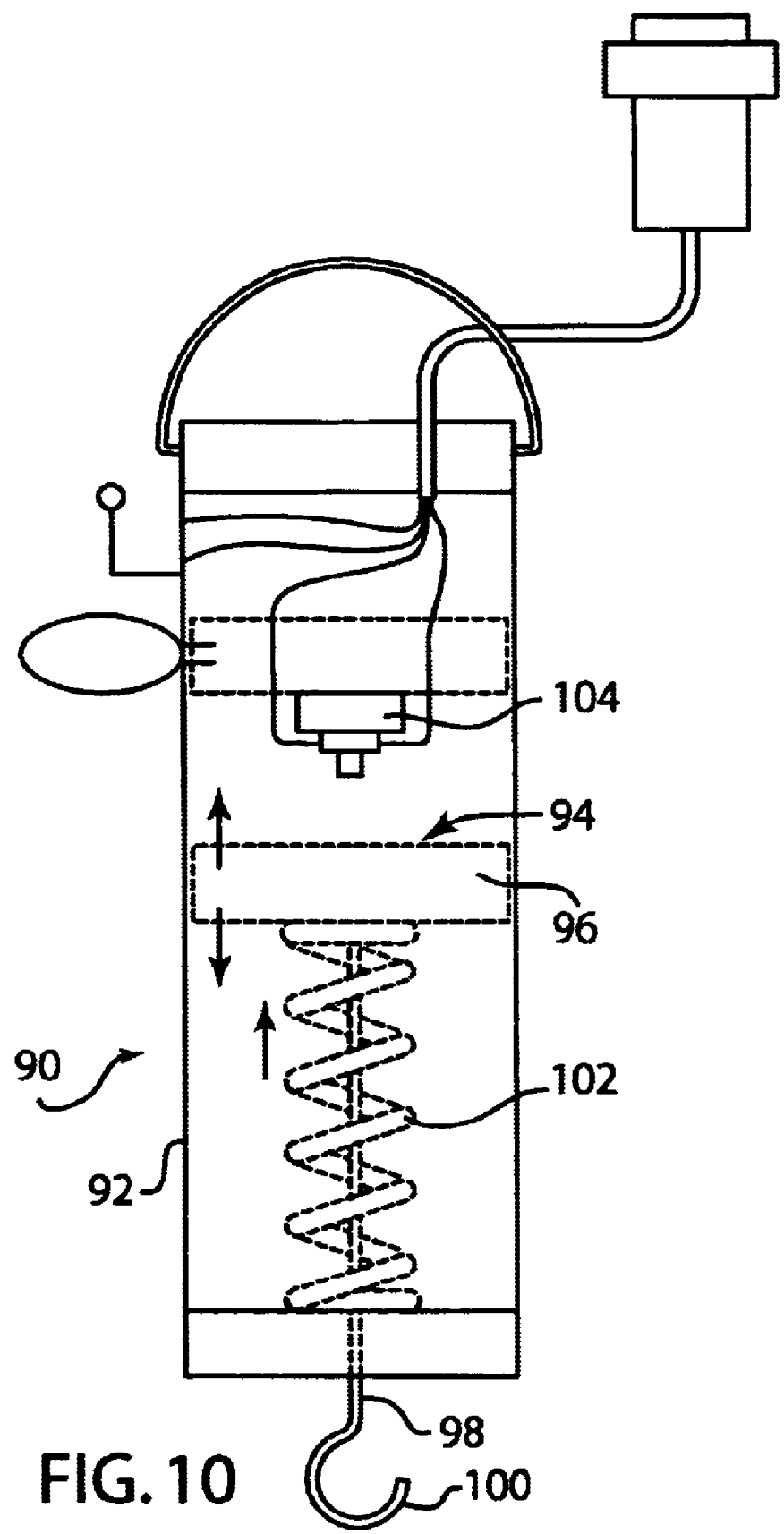
FIG. 10 is a schematic view of a mass level sensor for the patient monitor.

Infusion bag fluid level monitoring may be provided with a mass differential unit 90 such as is shown in FIG. 10. This type of sensor may also be used for any consumable. The fluid bag level sensor 90 preferably has a generally cylindrical housing 92. The housing 92 may be constructed of any suitable structural material, including metals, ceramics, and plastics, for example. The housing 92 may further be constructed by any appropriate method that is suitable for the material selected. The use of a cylindrical housing 92 may facilitate manufacture by extrusion, for example. Further, the cylindrical shape facilitates cleaning of the sensor.

As shown, the sensor 90 includes a plunger 94 that has a stop 96, a shaft 98, and a connector 100. The fluid sensor 90 will commonly be used by hanging the sensor on an I.V. pole or the like as is commonly known. The plunger 94 is slideably mounted in the cylinder 92 and slides between extended and retracted positions. A helical scale spring 102 or other scalable bias device urges the plunger 94 toward the retracted position. Further, a micro switch 104 or the like is preferably mounted to close a sensor circuit when the plunger 94 is in the retracted position. The plunger 94 extends when a mass, which may include an infusion fluid bag, is connected with the plunger by connecting the bag with the connector 100, which may be a hook, for example. Conversely, the bias 102 retracts the plunger 94 when the mass diminishes, indicating consumption of the infusion fluid or other consumable.

A trip level of the sensor 90, where the switch 104 is actuated, may be made adjustable. As shown, a position of the switch 104 may be adjustable relative to the spring 102 at 200 ml and 500 ml of infusion fluid, for example. The trip level of the sensor 90 relative to the content level of the infusion fluid is adjustable by relocating the position of the switch 104 along the cylinder 92, as will be understood by one having ordinary skill in the art.

Conversely, the structure of the sensor 90 may be inverted to sense an accumulation of a used fluid, for example, by either having the switch close when the plunger extends away from the switch 104 or by reprogramming the processor to accept an open switch 104 as a signal criteria. Further yet, the switch 104 may alternatively be placed to contact the plunger stop 96 and close the switch when the plunger is in the extended position. One having ordinary skill in the art will understand that these are only a few of many variations that may be used within the concept of the invention.

Another fluid accumulation sensor 120 that is useful with suction canisters and the like is shown in FIG. 11. The suction canister level sensor 120 has a plug or stopper 122 that cooperates with an opening in a top or cap of a suction canister. A pair of probes 124 and 126 extend in the same general direction from the stopper 122 and extend into a suction canister when the sensor is mounted for use. As fluid is accumulated in the suction canister, the fluid will make contact with the probes 124 and 126 and make a closed circuit condition that the processor may be programmed to interpret. The sensor 120 is connected with the processor by a cord 128, which may be removable from the stopper 122. Thus, the stopper 122 and probes 124 and 126 may be provided as a disposable part, while the cord 128 may be reusable.

The processor may be programmed to identify a variety of conditions relative to the position of the fluid along the probes 124 and 126. A full condition may be interpreted when the probes 124 and 126 are both first contacted by the fluid. Alternatively, the probes 124 and 126 may extend relatively far into the suction canister and a varying resistance between the probes as the fluid level rises may be interpreted by the processor as progressively greater quantities of fluid in the canister.

Figure 12:
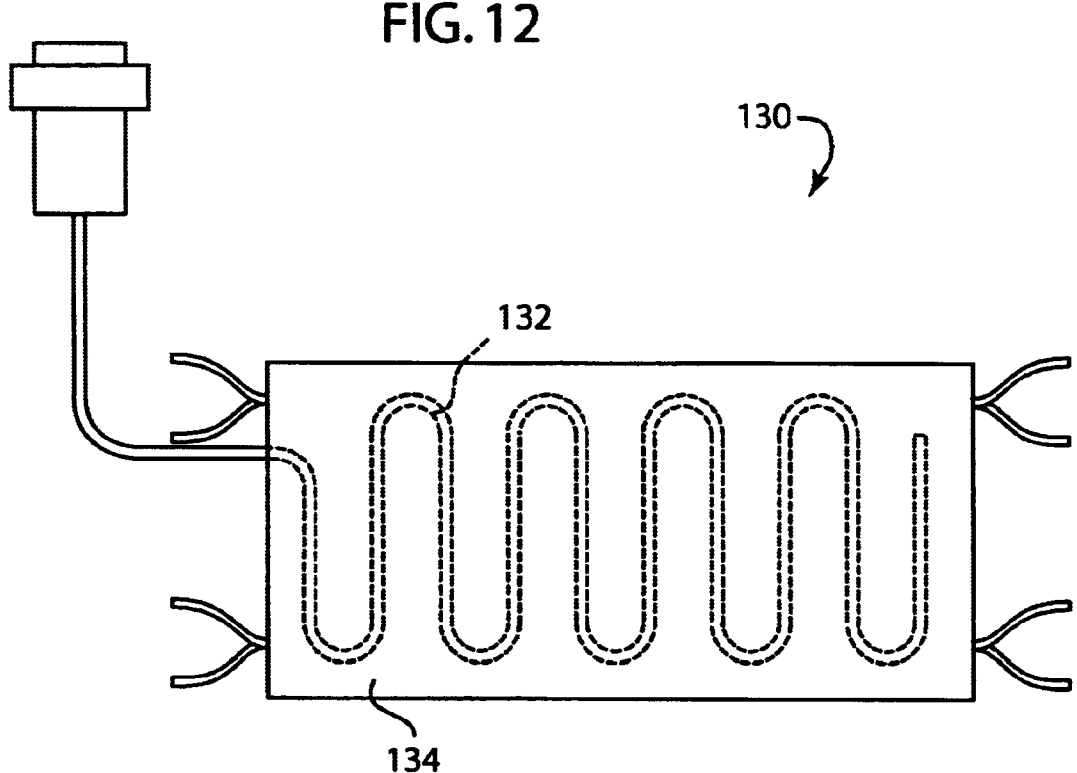
FIG. 12 is a schematic view of a patient movement pad for the patient monitor.

Another useful sensor 130 may include a patient motion sensor. The patient motion sensor 130 shown in FIG. 12 comprises a piezoelectric coaxial cable 132, for example. The cable 132 is threaded through a pad 134 that is placed under a patient. Electrical signals are generated by the piezoelectric cable 132 because of changes in pressure applied to the piezoelectric cable as the patient moves while laying upon the pad 134 and cable. Alternatively, if a more sophisticated motion sensor report is desired, a pad that has a touch sensitive grid may be used. Such a sensor may report specific body position and may be useful in a sleep study, for example.

Figure 13:
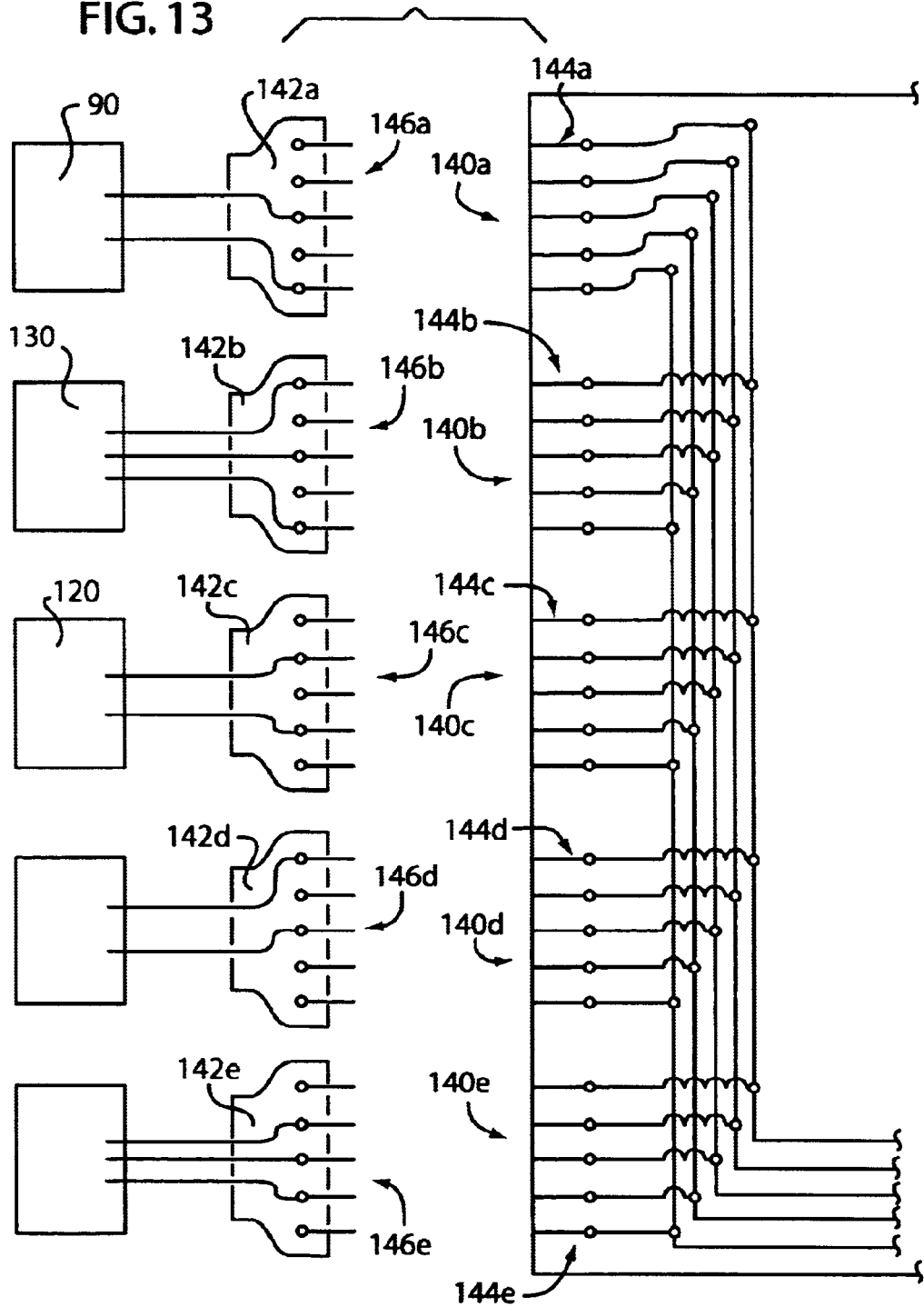
FIG. 13 is a schematic view of an array of connectors and input devices for the patient monitor.

The use of a wide variety of sensors is provided in the patient monitor by using keyed input sockets 140a–140e and plugs 142a–142e (FIG. 13). The cooperating input sockets 140a–140e and plugs 142a–142e are not sensor specific in that a different socket and plug combination are designated for each sensor. Rather, a socket 140a–140e and plug 142a–142e combination that has a plethora of connectors or contacts 144a–144e and 146a–146e, respectively, is used and a pattern or set of the contacts is identified with a particular sensor, resulting in a smart plug connection of the sensor with the processor. An exemplary schematic of five plugs 142a–142e and five sockets 140a–140e is shown in FIG. 13. Each plug 142a–142e and socket 140a–140e arbitrarily has five contacts 144a–144e and 146a–146e, respectively, as shown in FIG. 13. Significantly, any of the plugs 142a–142e can mate with any of the sockets 140a–140e. The sockets 140a–140e are conventionally connected in parallel, so the sockets are electrically identical. The distinction comes in how the socket contacts 144a–144e are connected with the processor and how the processor is programmed to interpret various signals from the contacts. One having ordinary skill in the art will understand that the processor may be programmed to discern and report as desired virtually any combination of contact input. Thus, a programming of the processor may dictate a plug wiring of the sensors or vice versa, a predetermined plug wiring of the sensors may dictate a programming of the processor.

As shown, the processor may be programmed to accommodate a plug 142a that has contacts 146a wired for a sensor 90 such as an infusion bag level empty sensor signal, while also accommodating a plug 142c that has contacts 146c wired for a sensor 120 such as a suction canister level full signal, for example. A plug 142b that has contacts 146b wired for a sensor 130 such as a piezoelectric motion sensor input may also be accommodated, for example. Other desired sensors may further be accommodated by differentiated wiring of contacts 146d and 146e of plugs 142d and 142e. Thus, the wiring of the sensor with the plug 142a–142e, and more particularly with the plug contacts 146a–146e and so with the processor through the socket contacts 144a–144e differentiates or identifies the particular sensor. A significant feature of this cooperating socket 140a–140e and plug 142a–142e arrangement is that the sensors and the processor may be configured so a preselected sensor can be plugged into any socket 140a–140e without a user wasting time or being distracted or otherwise being confused or making a mistake with regard to identifying the correct socket before plugging in a sensor.

It will be understood by one having ordinary skill in the art and by those who practice the invention, that various modifications and improvements may be made without departing from the spirit of the disclosed concept. Various relational terms, including left, right, front, back, top, and bottom, for example, are used in the detailed description of the invention and in the claims only to convey relative positioning of various elements of the claimed invention. The scope of protection afforded is to be determined by the claims and by the breadth of interpretation allowed by law.

I claim:

1. A patient monitoring device in combination with a fluid reservoir, comprising;
   a processing device;
   a display operatively connected with the processing device;
   a selector operatively connected with the processing device;
   a housing;
   at least one air pump mounted in the housing and operatively connected with the processing device, the air pump being adapted to provide at least one of air pressure and air suction;
   a fluid reservoir operatively connected with the air pump, the fluid reservoir being one of a fluid supply that is adapted to dispense a fluid when the air pump applies air pressure to the fluid supply and a suction canister that is adapted to collect fluid when the air pump applies a suction to the suction canister, respectively, the fluid reservoir being connected with the air pump so that fluid is precluded from drawing into the air pump;
   at least two sockets, each socket being substantially identical with a number of socket connectors, the sockets being electrically connected in parallel with one another, the socket connectors being operatively connected with the processing device;
   a first sensor, the first sensor being adapted to generate a signal according to a predefined criteria, the first sensor having a first sensor plug that corresponds to the at least two sockets whereby the first sensor plug removably couples with any of the at least two sockets, the first sensor plug having a set of first plug connectors that cooperates with the socket connectors, the first sensor being connected with fewer than all of the socket connectors when the first sensor plug is coupled with either of the at least two sockets and defining a first subset of the socket connectors, the first subset of the socket connectors being those socket connectors that connect with the first sensor when the first sensor plug is coupled with one of the at least two sockets; and
   a second sensor, the second sensor being adapted to generate a signal according to a predefined criteria, the second sensor having a second sensor plug that corresponds to the at least two sockets whereby the second sensor plug removably couples with any of the at least two sockets, the second sensor plug having a set of second plug connectors that cooperates with the socket connectors, the second sensor being connected with fewer than all of the socket connectors when the second sensor plug is coupled with either of the at least two sockets and defining a second subset of the socket connectors, the second subset of the socket connectors being those socket connectors that connect with the second sensor when the second sensor plug is coupled with one of the at least two sockets, the second subset of the socket connectors also being a different subset from the first subset of the socket connectors.

2. A method of monitoring a patient comprising the steps of:
   providing a sensor that is adapted to generate a sensor signal according to a predefined criteria;
   providing a programmable processing device that is adapted to respond to the sensor signal, the programmable processing device having at least a first register, the programmable processing device having at least a first interface port;

providing a power supply for the programmable processing device, the power supply having a power switch by which the programmable processing device is switched between off and on conditions;

providing a housing;

providing an air pump, the air pump being adapted to provide at least one of air pressure and air suction;

providing a fluid reservoir, the fluid reservoir being one of a fluid supply that is adapted to dispense a fluid when the air pump applies air pressure to the fluid supply and a suction canister that is adapted to collect fluid when the air pump applies a suction to the suction canister, respectively;

operatively connecting the air pump and the fluid reservoir, the fluid reservoir being connected with the air pump so that fluid is precluded from drawing into the air pump;

operatively connecting the fluid pump with the processing device;

operatively connecting the sensor with the first interface port;

configuring the processing device to respond to switching from the off condition to the on condition by setting the first register to predetermined reference values;

configuring the processing device to perform a diagnostic test of the processing device in accordance with predetermined criteria;

configuring the processing device to poll the first interface port and record a status of the first interface port;

configuring the processing device with a table of boundary values for the first interface port;

configuring the processing device to compare the status of the first interface port with the table of boundary values, further configuring the processing device to generate an alarm signal when the status of the first interface port is outside the table of boundary values;

providing an alarm, the alarm being one of a group of alarms that includes a visual indicator and an audible indicator the alarm further being responsive to the alarm signal; and providing a user control interface and operatively connecting the user control interface with the processing device whereby at least the table of boundary values for the first interface port are variable by a user.

* * * * *